US009927722B2

(12) United States Patent
Van Berkel et al.

(10) Patent No.: US 9,927,722 B2
(45) Date of Patent: Mar. 27, 2018

(54) METHOD AND APPARATUS FOR INSPECTION AND METROLOGY

(71) Applicant: ASML NETHERLANDS B.V., Veldhoven (NL)

(72) Inventors: Koos Van Berkel, Waalre (NL); Duygu Akbulut, Eindhoven (NL); Jeroen Johan Maarten Van De Wijdeven, Eindhoven (NL); Ferry Zijp, Nuenen (NL)

(73) Assignee: ASML NETHERLANDS B.V., Veldhoven (NL)

( * ) Notice: Subject to any disclaimer, the term of this patent is extended or adjusted under 35 U.S.C. 154(b) by 14 days.

(21) Appl. No.: 15/052,201

(22) Filed: Feb. 24, 2016

(65) Prior Publication Data

US 2016/0246189 A1    Aug. 25, 2016

(30) Foreign Application Priority Data

Feb. 25, 2015  (EP) .................................... 15156499

(51) Int. Cl.
| | |
|---|---|
| *G03F 7/20* | (2006.01) |
| *G03F 9/00* | (2006.01) |
| *G02B 21/00* | (2006.01) |
| *G01N 21/956* | (2006.01) |

(52) U.S. Cl.
CPC ....... *G03F 7/70775* (2013.01); *G01N 21/956* (2013.01); *G02B 21/0016* (2013.01); *G03F 7/70625* (2013.01); *G03F 7/70633* (2013.01); *G03F 9/7019* (2013.01)

(58) Field of Classification Search
CPC ............. G03F 7/70775; G03F 7/70633; G03F 7/70625

USPC .............................................. 355/52, 53, 55
See application file for complete search history.

(56) References Cited

U.S. PATENT DOCUMENTS

| | | | |
|---|---|---|---|
| 5,354,985 | A | 10/1994 | Quate |
| 5,939,709 | A | 8/1999 | Ghislain et al. |
| 6,441,359 | B1 | 8/2002 | Cozier et al. |
| 7,791,732 | B2 | 9/2010 | Den Boef et al. |
| 7,826,317 | B2 | 11/2010 | Ishimoto |
| 7,933,177 | B2 | 4/2011 | Ishimoto |
| 8,411,287 | B2 | 4/2013 | Smilde et al. |
| 8,902,403 | B2 | 12/2014 | Leenders et al. |

(Continued)

FOREIGN PATENT DOCUMENTS

| | | |
|---|---|---|
| CN | 102483582 | 5/2012 |
| TW | 201232060 | 8/2012 |
| WO | 2016/030227 | 3/2016 |

OTHER PUBLICATIONS

International Search Report and Written Opinion dated Sep. 13, 2016 in corresponding International Patent Application No. PCT/EP2016/053809. S. Blanvillain et al., "Pull-in control during nanometric positioning by near field position sensing," Proceedings of 47th IEEE Conference on Decision and Control, Cancun, Mexico, pp. 5194-5199 (Dec. 9-11, 2008).

(Continued)

*Primary Examiner* — Hung Henry Nguyen
(74) *Attorney, Agent, or Firm* — Pillsbury Winthrop Shaw Pittman LLP

(57) ABSTRACT

A method and apparatus for position control of a component relative to a surface is disclosed. The method may include calculating an estimated effect of, or derived from, Casimir force acting between the component and the surface, and compensating positioning of the component relative to the surface using the estimated effect.

26 Claims, 10 Drawing Sheets

(56) References Cited

U.S. PATENT DOCUMENTS

| | | | |
|---|---|---|---|
| 9,081,303 B2 | 7/2015 | Cramer et al. | |
| 2002/0029609 A1* | 3/2002 | Johnston | G01B 7/14 73/1.49 |
| 2006/0066855 A1 | 3/2006 | Boef et al. | |
| 2008/0037380 A1 | 2/2008 | Ishimoto | |
| 2009/0040906 A1 | 2/2009 | Hong et al. | |
| 2009/0185306 A1 | 7/2009 | Park et al. | |
| 2009/0245054 A1 | 10/2009 | Verschuren | |
| 2010/0118684 A1 | 5/2010 | Horikawa et al. | |
| 2011/0027704 A1 | 2/2011 | Cramer et al. | |
| 2011/0043791 A1 | 2/2011 | Smilde et al. | |
| 2011/0261662 A1 | 10/2011 | Hsieh | |
| 2011/0273687 A1 | 11/2011 | Leenders et al. | |
| 2012/0044470 A1 | 2/2012 | Smilde et al. | |
| 2013/0342831 A1 | 12/2013 | Levinski et al. | |

OTHER PUBLICATIONS

Anonymous, "Atomic-force microscopy," Wikipedia, the free encyclopedia, https://en.wikipedia.org/w/index.php?title=Atomic-force_microscopy&oldid=645686100, pp. 1-12 (downloaded Jun. 28, 2016).

Taiwan Office Action dated Dec. 12, 2016 in corresponding Taiwan Patent Application No. 105105731.

Geon Lim et al., "Improved Nanogap Servo System Using an Error-Based Disturbance Observer for High-Speed in Solid Immersion Lens-Based Plasmonic Lithography," Jpn. J. Appl. Phys., vol. 52, pp. 09LG02-1-09LG02-8 (2013).

Alejandro W. Rodriguez et al., "The Casimir effect in microstructured geometries," Nature Photonics, vol. 5, pp. 211-221 Apr. 2011).

* cited by examiner

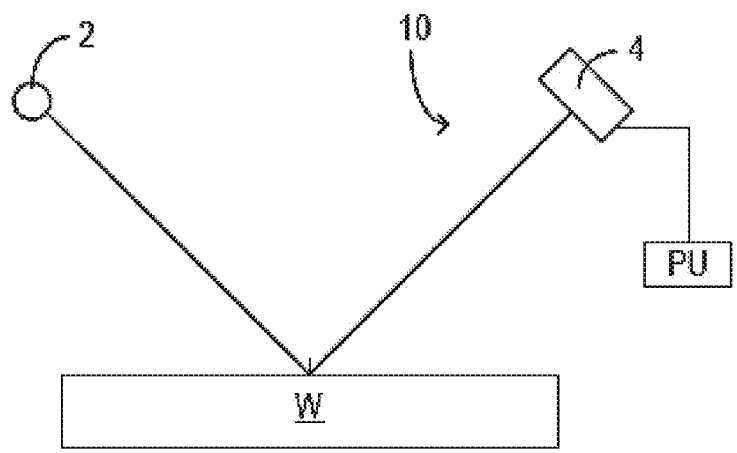
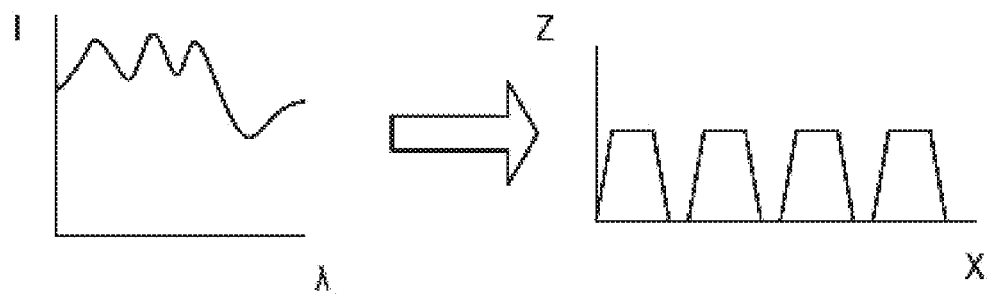
Fig. 3

METHOD AND APPARATUS FOR INSPECTION AND METROLOGY

This application claims priority to European patent application no. 15156499.4, filed Feb. 25, 2015, which is incorporated herein in its entirety by reference.

FIELD

The present description relates to a method and apparatus to control a distance between two objects.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, the patterned substrate is inspected and one or more parameters of the patterned substrate are measured. The one or more parameters may include, for example, the overlay error between successive layers formed in or on the patterned substrate and/or critical linewidth of developed photosensitive resist. This measurement may be performed on a target of the product substrate itself and/or on a dedicated metrology/inspection target provided on the substrate. There are various techniques for making measurements of the microscopic structures formed in lithographic processes, including the use of a scanning electron microscope and/or various specialized tools.

A fast and non-invasive form of specialized inspection tool is a scatterometer in which a beam of radiation is directed onto a target on the surface of the substrate and properties of the scattered or reflected beam are measured. By comparing one or more properties of the beam before and after it has been reflected or scattered by the substrate, one or more properties of the substrate can be determined. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a relatively narrowband radiation beam and measures the intensity of the scattered radiation as a function of angle.

A particular application of scatterometry is in the measurement of feature asymmetry within a periodic target. This can be used as a measure of overlay error, for example, but other applications are also known. In an angle resolved scatterometer, asymmetry can be measured by comparing opposite parts of the diffraction spectrum (for example, comparing the −1st and +$1^{st}$ orders in the diffraction spectrum of a periodic grating). This can be done simply in angle-resolved scatterometry, as is described for example in U.S. patent application publication US2006-066855.

SUMMARY

With reduction of the physical dimensions in lithographic processing, there is demand to, for example, increase measurement accuracy and/or reduce the space occupied by targets dedicated to metrology/inspection. Image based scatterometry measurements have been devised to allow the use of smaller targets, by taking separate images of the target using −$1^{st}$ and +$1^{st}$ order radiation in turn. Examples of this image based technique are described in published U.S. patent application publication nos. US2011-0027704, US2011-0043791 and US2012-0044470, which are incorporated herein in their entirety by reference Demand for further reduction in target size and for improved accuracy continues, however, and existing techniques suffer from various constraints that make it difficult to maintain accuracy and/or reduce the size of the targets. Another way to improve on inspection and measurement techniques is to use a solid immersion lens (SIL) as the optical element nearest the substrate surface. The extreme proximity of the SIL with the substrate surface (e.g., target surface) results in near-field radiation with a very high effective numerical aperture (NA) larger than 1. Using a coherent radiation source with this SIL allows a very small target to be inspected.

To take advantage of the increasing numerical aperture, the gap between the SIL and the substrate needs to be set to a desired value. For example, the gap may be within the range of $\lambda/40$ to $\lambda/8$ (where $\lambda$ is the wavelength of the measurement radiation) to have the SIL in effective optical contact with the substrate. An example optical gap measuring method and apparatus can involve detecting cross components of polarization in the high numerical aperture element. The cross polarized signal is then recorded by a detector and can be used as an input parameter into a gap control process. This cross polarized signal may also be normalized by the cross polarized signal detected at a large gap of several wavelengths. In another example, the gap may be controlled by reference to reflected laser radiation intensity. With any detecting method, the gap between the SIL (or other component) and the substrate (or other surface) needs to be established to be, and maintained at, a desired gap distance or distance range.

With such small gap distances and various surface topographies possible (whether expected or unexpected due to process variations), it is desired to provide one or more methods and apparatus to control the position of a component relative to a surface at solid immersion gap distances. So, as a particular application, an embodiment may be applied to controlling a gap between an optical element and a reflective or diffractive surface for, e.g., inspection of a layer manufactured by a lithographic technique to measure overlay error or other one or more other parameters.

In an aspect, there is provided a method of position control of a component relative to a surface, the method comprising: calculating an estimated effect of, or derived from, Casimir force acting between the component and the surface; and compensating positioning of the component relative to the surface using the estimated effect.

In an aspect, there is provided a method of position control of a component relative to a surface, the method comprising: generating a trigger signal from a measured signal in a control loop of the component, or from a signal derived from the measured signal in the control loop; and evaluating whether the trigger signal passes a threshold to determine proximity of the component to the surface. In an embodiment, generating the trigger signal comprises generating the trigger signal from a control error signal, the control error signal being a measure of the difference in a measured gap between the component and the surface and a desired gap between the component and the surface.

In an aspect, there is provided a method, comprising: for a value of a Casimir and/or electrostatic force or stiffness that destabilizes a control signal for positioning a component relative to a surface, calculating an estimated gap distance between the component and the surface based on Casimir and/or electrostatic force or stiffness between the component and the surface; evaluating a gap signal related to a gap distance between the component and the surface to identify an instability in the gap signal, the gap distance at the instability being a reference gap distance; and evaluating the reference gap distance against the estimated gap distance to arrive at a correction factor for positioning of the component relative to the surface.

In an aspect, there is provided a method of position control of a component relative to a surface, the method comprising: calculating an estimated effect of Casimir stiffness acting between the component and the surface based on a measured gap distance between the component and the surface; and using the estimated effect of Casimir stiffness to compensate actual Casimir stiffness of the positioning of the component relative to the surface.

BRIEF DESCRIPTION OF THE DRAWINGS

Embodiments will now be described, by way of example only, with reference to the accompanying drawings in which:

FIG. 3 schematically depicts an example inspection apparatus and metrology technique;

DETAILED DESCRIPTION

Before describing embodiments in detail, it is instructive to present an example environment in which embodiments may be implemented.

Figure 1:
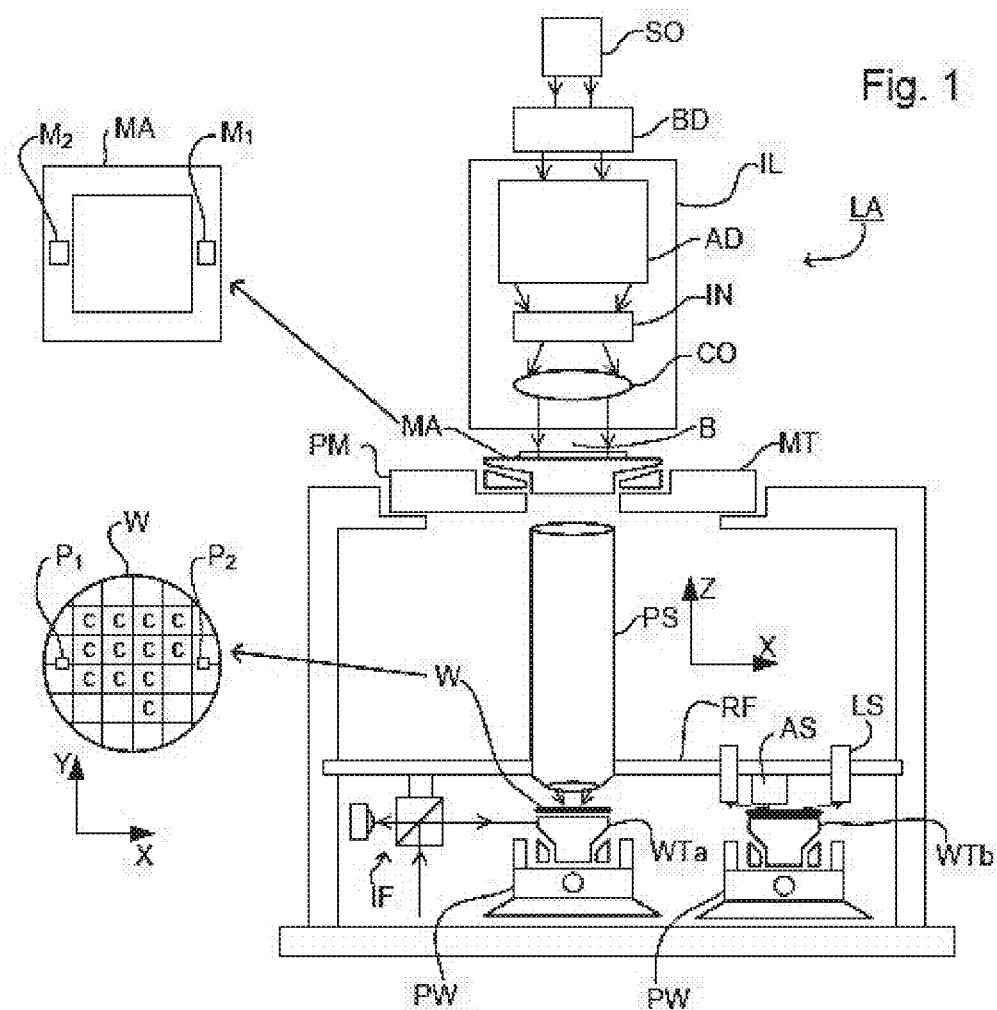
FIG. 1 schematically depicts an embodiment of a lithographic apparatus.

FIG. 1 schematically depicts a lithographic apparatus LA. The apparatus comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters; and
- a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, deformable mirrors, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated, to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are known in the art for increasing the numerical aperture of projection systems. The term "liquid immersion" as used herein does not mean that a structure, such as a substrate, must be submerged in liquid, but rather only means that liquid is located between the projection system and the substrate during exposure.

Further, the lithographic apparatus may also be of a type wherein at least an optical element is located in close proximity to a portion of the substrate resulting in near-field radiation spanning a gap between the optical element and the substrate. This may be referred to as solid immersion using a solid immersion lens/optical element.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
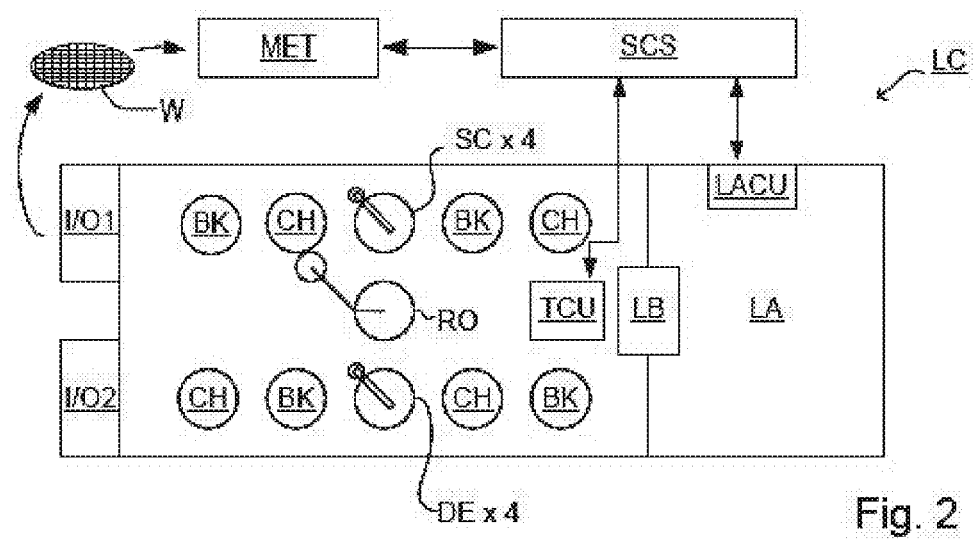
FIG. 2 schematically depicts an embodiment of a lithographic cell or cluster.

As shown in FIG. 2, the lithographic apparatus LA forms part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure one or more properties such as overlay error between subsequent layers, line thickness, critical dimension (CD), etc. Accordingly a manufacturing facility in which lithocell LC is located also typically includes a metrology/inspection system MET which receives some or all of the substrates W that have been processed in the lithocell. The metrology/inspection system MET may be part of the lithocell LC, for example it may be part of the lithographic apparatus LA.

Metrology/inspection results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology/inspection system MET, an inspection apparatus is used to determine one or more properties of the substrate, and in particular, how one or more properties of different substrates vary or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after the exposure. However, the latent image in the resist has a low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

FIG. 3 depicts an example inspection apparatus (e.g., a scatterometer). It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some parameters are assumed from knowledge of the process by which the structure was made, leaving only a few parameters of the structure to be determined from the measured data. Such an inspection apparatus may be configured as a normal-incidence inspection apparatus or an oblique-incidence inspection apparatus.

Figure 4:
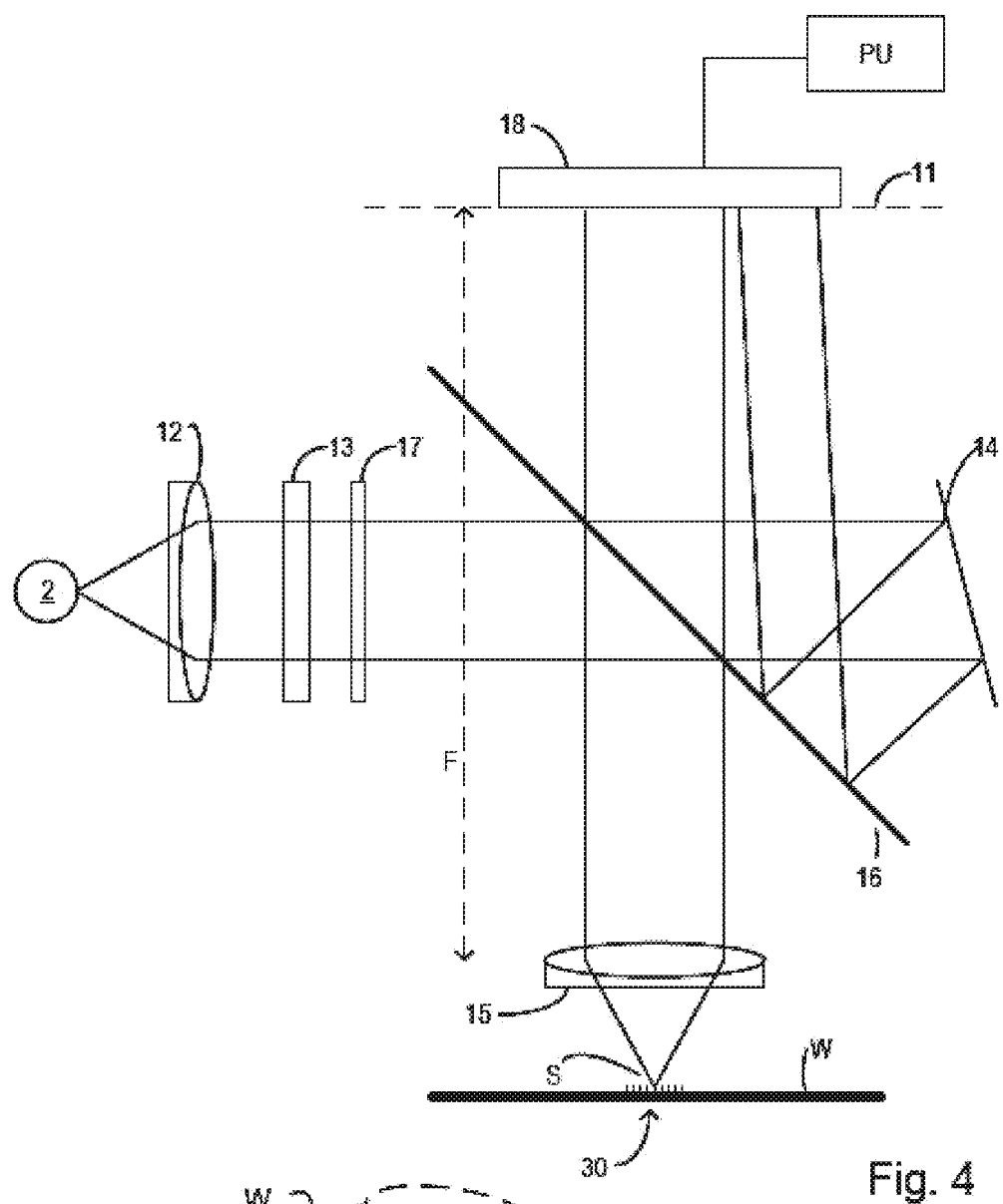
FIG. 4 schematically depicts an example inspection apparatus.

Another inspection apparatus that may be used is shown in FIG. 4. In this device, the radiation emitted by radiation source 2 is collimated using lens system 12 and transmitted through interference filter 13 and polarizer 17, reflected by partially reflecting surface 16 and is focused into a spot S on substrate W via an objective lens 15, which has a high numerical aperture (NA), desirably at least 0.9 or at least 0.95. A solid immersion inspection apparatus (using near-field radiation between an objective of the apparatus and the target) and/or a liquid immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 16 into a detector 18 in order to have the spectrum detected. The detector may be located in a back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector may be a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

One or more interference filters 13 are available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 18 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into the substrate. The pattern (e.g., of bars, pillars or vias) is sensitive to chromatic aberration in the lithographic projection apparatus, particularly the projection system PS, and illumination symmetry and the presence of such aberration will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step and/or other inspection processes.

In addition to measurement of a parameter by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of FIG. 3 or FIG. 4 are described, for example, in U.S. patent application publication US2006-066855, which is incorporated herein in its entirety. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

Figure 5:
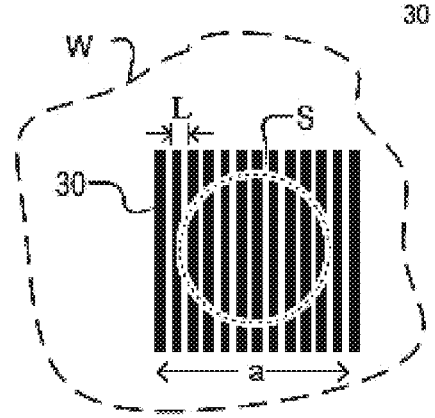
FIG. 5 illustrates the relationship between an illumination spot of an inspection apparatus and a metrology/inspection target.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be over 10 or 20 µm and the target width a and length may be 30 or 40 µm square. The target in other words is 'underfilled' by the illumination, and the diffraction signal is free from interference by product features and the like outside the target itself. The illumination arrangement 2, 12, 13, 17 may be configured to provide illumination of a uniform intensity across a pupil plane of objective 15. Alternatively, by, e.g., including an aperture in the illumination path, illumination may be restricted to on axis or off axis directions.

In recent times, there is demand from users to reduce the space occupied by metrology/inspection targets and/or to improve the accuracy of the measurements. In particular, there is a desire to reduce the width of 'scribe lanes' between target portions C on the substrate, where the targets have conventionally been located. Moreover, there is a desire to include targets within the device patterns themselves, to allow more accurate monitoring and correction of variations in parameters such as CD and/or overlay. To this end, alternative methods of diffraction based metrology/inspection have been devised more recently. For example, in image-based metrology/inspection, two images of the target are made, each using different selected orders of the diffraction spectrum. Comparing the two images, one can obtain asymmetry information. By selecting parts of the images, one can separate the target signal from its surroundings. The targets can be made smaller, and need not be square, so that several can be included within the same illumination spot.

Examples of this technique are described in U.S. patent application publications US2011-0027704, US2011-0043791, and US2012-0044470.

As the demand for size reduction and/or accuracy continues, existing techniques may meet some technical limitations. For example, some methods (e.g., overlay measurement methods) may need to capture at least the ±1$^{st}$ diffraction orders. Taking into account the numerical aperture of the objective 15, this constrains the pitch (L) of a periodic structure of the target. To improve sensitivity and/or to reduce target size, one can consider using shorter wavelengths. In practice, however, the illumination wavelength has to be in visible range because in an overlay target a lower periodic structure may be deeply buried and one or more intervening layers may absorb UV radiation (200 nm to 400 nm). Further, the target cannot be too small otherwise it will not have enough features to be considered as a periodic structure (e.g., at least 15 lines may be required which taking into account previous constraints may fix the minimum periodic structure size around 5 µm×5 µm). Consequently, overlay, as an example, is measured using periodic structures features (e.g., lines) having dimensions far bigger than those of the product (e.g., device) layout, making overlay measurement less reliable. Ideally the feature line and pitch should have similar dimensions to the product features.

Figure 6:
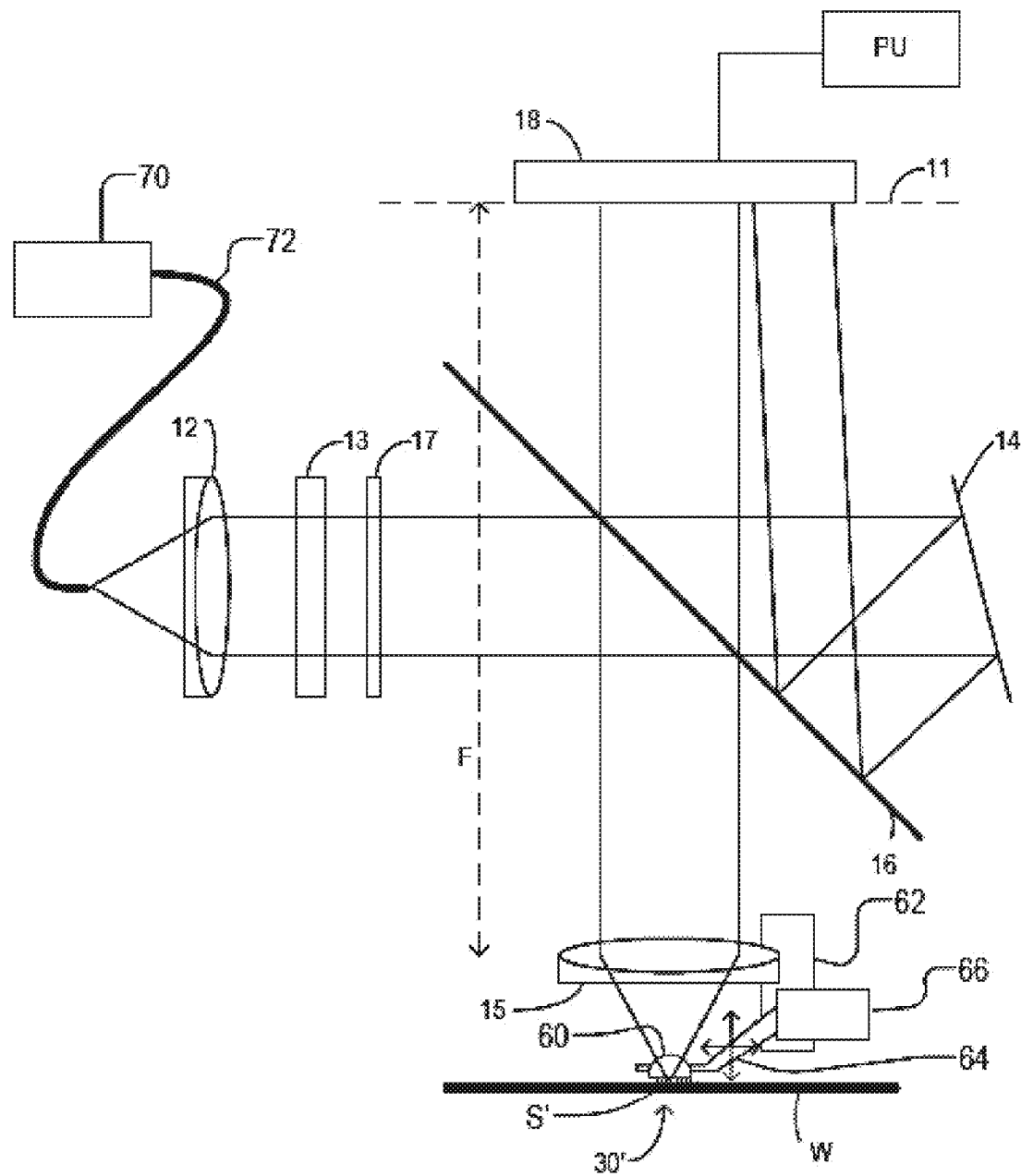
FIG. 6 depicts an example inspection apparatus comprising a solid immersion lens (SIL)

FIG. 6 shows an inspection apparatus in which a smaller spot S' of illumination can be applied to a smaller target 30', which has features of smaller pitch. Like reference numerals refer to like components throughout the figures.

Comparing the apparatus of FIG. 6 with that of FIG. 4, a first difference is the provision of an additional lens element 60 close to the target 30'. This additional lens is a miniature solid immersion lens (SIL), with a width (e.g., diameter) only on the order of a millimeter, for example in the range of 1 mm to 5 mm, for example about 2 mm. The SIL comprises, in an example, a hemisphere or super-hemisphere of material that receives rays of radiation at substantially normal incidence to its surface. In an embodiment, the SIL is made up of a material of refractive index n, such as glass, fused quartz, a combination of materials, etc. The received rays come to focus at about the center of the hemisphere or super-hemisphere and form a diffraction-limited spot that is smaller by a factor of n compared to what would have been in the absence of the SIL. For example, a typical glass hemisphere having n=2 will reduce the width of the focused spot by a factor of 2.

Immersion of optical elements in liquid has been used to increase resolution in microscopy and photolithography. The solid immersion lens may achieve similar gains without the inconvenience/problems of liquid immersion. However, to ensure that the smaller spot size does indeed increase the resolution of the system, the bottom of the SIL must either be in contact with the target 30 or positioned extremely closely to it. This restricts its practical applications.

A so-called micro-SIL may also be used. The width (e.g., diameter) of such a SIL is many times smaller, for example about 2 microns in width instead of about 2 millimeters. In an example where SIL 60 in the FIG. 6 apparatus is a micro-SIL, it may have a width (e.g., diameter) less than or equal to 10 µm, potentially less than or equal to 5 µm.

Whether a miniature SIL 60 or a micro-SIL lens is used, it can be attached to a movable support so that controlling the alignment and proximity to the substrate is much simpler than in the case of a lens with bigger width. For example, the SIL 60 in FIG. 6 is mounted to a frame 62. In an embodiment, frame 62 is movable. An actuator may be provided to move frame 62. In an embodiment, the frame 62 supports the objective 15. Accordingly, in an embodiment, the frame 62 may move both the objective 15 and the SIL 60 together. In an embodiment, the actuator for the frame 62 may be configured to move the frame 62 (and the SIL 60) in substantially the Z direction. In an embodiment, the actuator for the frame 62 may be configured to move the frame 62 (and the SIL 60) around the X axis and/or Y axis. In an embodiment, the SIL 60 is in relative fixed position relative to the frame 62. This may be referred to a single stage arrangement, where the objective 15 and SIL 60 are fixed relative to each and are moved by the actuator of frame 62. In such a case, a benefit may be that the SIL can be mechanically positioned in the focus of the objective.

As noted above, the SIL 60 in FIG. 6 is mounted to a frame 62, which in an embodiment supports objective 15. Of course, the SIL 60 may be mounted on a separate frame from that supporting objective 15. In an embodiment, the SIL 60 is connected to a frame (e.g., frame 62) via an arm 64 and actuator 66. Actuator 66 may be, for example, piezoelectric in operation or voice coil actuated. The arrangement where the SIL 60 has an actuator to cause relative movement between a movable objective 15 and the SIL 60 may be referred to as a dual stage arrangement. In a dual stage, certain functionalities may be separated, e.g. separation of motion ranges, vibration suppression capabilities, SIL positioning and focusing with respect to the surface. In an embodiment, the objective stage may move only substantially in the Z-direction (substantially normal to the surface). In an embodiment, the SIL stage may move in more than 1 degree of freedom, e.g., at least 3 degrees of freedom, e.g., in the Z-direction and about the X-axis and/or the Y-axis, to position the SIL substantially parallel to the surface. The SIL stage may not have a mechanical range sufficient to cover the desired full travel range. So, the SIL stage can be used to position the SIL at a certain small distance above the surface, while the objective stage can position the objective at focus with respect to the surface.

Actuator 66 may operate in combination with one or more other actuators positioning the objective as a whole in relation to the target. In relation to the coarse and fine positioners mentioned above, for example, the actuator 66 may be regarded as an ultra-fine positioner. The servo control loops of these different positioners can be integrated with one another. The components 62, 64 and 66, together with the substrate table and positioners (mentioned above but not shown in FIG. 6), form a support apparatus for positioning the SIL and the target T in close proximity to one another. As noted above, in principle, SIL 60 could be mounted rigidly to the frame 62, and/or may be of larger width. The separate arm and actuator allows easier control of the very small gap, as discussed in more detail below.

Inclusion of the SIL 60 opens the possibility of focusing to a much smaller spot S'. The SIL works by capturing the near-field radiation from the target, and to this end it is positioned substantially closer than one wavelength (λ) of radiation from the target structure, generally closer than a half wavelength, for example around λ/20. The closer the distance, the stronger will be the coupling of near-field signals into the instrument. The gap between the SIL 60 and target 30' may therefore be less than λ/4, for example between λ/40 and λ/8. Because the NA of the inspection apparatus is effectively increased, the pitch of the target periodic structure may be reduced closer to product dimensions.

In examples where a micro-SIL would be used, incoherent radiation of the type conventionally used in, for example, a scatterometer cannot be focused to a micron-sized spot as small as the micro-SIL. Accordingly, in such an embodiment the radiation source 2 may be changed to a coherent source. Therefore a laser source 70 is coupled to illumination optics 12, etc. via an optical fiber 72. The limit on the spot size on the substrate is set by the numerical aperture of the focusing lens system and the laser wavelength. As an additional benefit of using spatially coherent radiation, the instrument with laser radiation source 70 can be used to perform different types of scatterometry or measurement. For example, coherent Fourier scatterometry (CFS) may be used to measure the target.

As highlighted above, a small gap should be maintained between the SIL and the target. As also highlighted above, known techniques for controlling the gap have limitations, particularly when a variety of different target structures and materials are to be inspected.

Accordingly, in an embodiment, it is proposed to control the gap by a technique based on compensating an attractive forces between the SIL and the target. The technique has particular applicability in an optical metrology/inspection apparatus such as a scatterometer, but can be applied in other applications of SILs or in other applications where an object is positioned and/or maintained very close to another object (e.g., in the below 400 nm range). The technique need not be applied exclusively, and could be applied in combination with one or more other techniques, including one or more techniques discussed in the cited documents.

As the gap between two solid surfaces decreases, a generalized version of van der Waals forces arises between the two surfaces due to quantum fluctuations of the electromagnetic field. This generalized version of van der Waals forces is known as a Casimir force and is an attracting force between the two surfaces. Van der Waals forces arise when two neutral particles have fluctuating dipole moments resulting from quantum or thermal effects, and vary based on separation distance between the particles.

So, for perfectly conducting, parallel plates, this Van der Waals interaction results in an approximate attractive Casimir force given by the equation:

$$F_{cas} = \frac{hc\pi^2 A}{240z^4} \quad \text{Equation (1)}$$

where h is the reduced Planck's constant, and is equal to $h/2\pi$, h being the Planck's constant=6.624 $e^{-34}$ Js, c is the speed of light ($3e^8$ m/s), A is the area of SIL tip surface in proximity to the target surface, and z is the gap separating the SIL tip surface from the target surface. Note, as discussed below, the result from Equation (1) may need to be varied to account for different materials, different topography, etc. Moreover, at very small separations of the two plates (e.g., up to about several 100 nanometers), the force can scale at $1/z^3$ instead of $1/z^4$. See, e.g., A. Rodriguez et al., "The Casimir effect in microstructured geometries", Nature Photonics, Vol. 5, pages 211-221 (2011), incorporated by reference herein in its entirety. Further, it is expected that, due to the complexity of the proximity interactions, the force scales with a non-integer power law, such that the force would be proportional to $1/z^n$, with $2.5 \leq n \leq 5.5$, in the most general expression.

This approximate attractive Casimir force can be further expressed as being a result of a spring having a stiffness $k_{cas}$ given by:

$$k_{cas}(z) = \frac{\partial F_{cas}}{\partial z} = -\frac{hc\pi^2 A}{60z^5} \quad \text{Equation (2)}$$

Apart from the Casimir force and stiffness given by Equations (1) and (2) above, force and stiffness due to electrostatic interaction also becomes significant at such small gaps. For electrostatic force between perfectly conducting, parallel plates, the electrostatic force between the SIL tip surface and a target surface is approximately given by:

$$F_{es} = \frac{\epsilon_0 A V^2}{2z^2} \quad \text{Equation (3)}$$

where V is the voltage difference between the SIL tip surface and the target surface, z is the gap separating the SIL tip surface from the target surface, surface, A is the area of SIL tip surface in proximity to the target surface, and $\epsilon_0 = 8.85e^{-12}$ Farad/m. The electrostatic stiffness is therefore:

$$k_{es}(z) = \frac{\partial F_{es}}{\partial z} = -\frac{\epsilon_0 A V^2}{z^3} \quad \text{Equation (4)}$$

Because of the power law, as z decreases, the Casimir stiffness overshadows the electrostatic stiffness. For applications such as near-field metrology/inspection where the z is on the order of $\lambda/40-\lambda/20$, which may be around 10-30 nm, and V is small, the electrostatic stiffness may become negligible compared to the Casimir stiffness.

Further, it should be recognized that the physics governing the environment between the SIL tip surface and the target surface is very complex. For example, it could be that, in specific circumstances, an electro-magnetic stiffness, due to a plethora of electro-magnetic related forces between the SIL tip surface and the target surface, overshadows the Casimir stiffness. At higher voltages, an example of said electro-magnetic force is the capacitive force between the SIL tip and the target surface. Another example of said electro-magnetic forces is due to existence of random patch charges. Yet another example of said electro-magnetic force is due to static charges present on non-metallic surface (for example, charge-charge, charge-dipole, dipole-dipole). Such electrostatic force, due to static charges, is considered to be difficult to predict and it is probably strongly dependent on the fabrication process of the target surface. Yet another example of electro-magnetic interaction is due to the presence, on the SIL tip surface and/or target surface, of polar liquids, for example water. Such presence of polar liquids is further affected by the type of surfaces in relation to fluids, such as hydrophilic or hydrophobic surfaces. Therefore, most generally, one has proximity forces acting between the SIL tip surface and the target surface, proximity forces comprising the Casimir forces, or electro-magnetic forces, for example.

Further, for practical SIL dimensions, microscopic forces, such as the electrostatic and Casimir force, between the SIL and target surface become noticeable at gaps of around 10-30 nm (e.g., $\lambda/40-\lambda/20$). These forces are typically negligible compared to the control forces. However, as described further below, the stiffness (force-distance gradient) can exceed a control stiffness due to highly non-linear characteristics of these microscopic forces, and so destabilize a control loop.

Figure 7A:
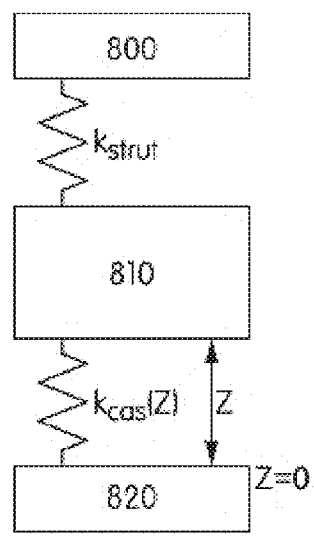
FIG. 7(A) depicts a schematic spring diagram of specific components of an inspection apparatus in relation to a target surface.

FIG. 7(A) depicts a schematic representation of the relationship between specific components of the inspection apparatus and the target surface (e.g., substrate). As seen in FIG. 7(A), the objective (e.g., objective 15) or other frame 800 of the inspection apparatus has connected thereto a movable SIL 810, wherein the stiffness between the objective and the SIL is designated as $K_{strut}$. The SIL 810 is movable relative to the target surface (e.g., substrate) 820 at least in the vertical direction to establish a gap Z. The Casimir stiffness (which varies as a function of the gap distance Z) between the SIL and the target surface is designated as $K_{cas}(z)$. Here, the electrostatic force and stiffness is ignored but may be included as an additional force and stiffness element in FIG. 7(A).

A control system is provided to control positioning of the SIL close to the target surface and to maintain the SIL at or around that position. The control system may receive a setpoint gap value and control one or more actuators (e.g., actuator 66) to position the SIL at or near the setpoint gap value and maintain the SIL at or around that position. In such a system, a gap between the SIL and the target surface may be maintained at approximately $\lambda/20$. The relative vibrations between the target surface and the SIL holder (e.g., the objective) may be on the order of $\lambda/4$, which can be, e.g., suppressed by means of relatively high bandwidth feedback control, e.g., with a bandwidth between 1 kHz and 20 kHz, for example 10 kHz. To enable the control by the control system, the gap between the SIL and the target surface may be represented by an optical signal called gap error signal (GES). Various techniques for measuring the GES are known in the art.

Figure 8B:
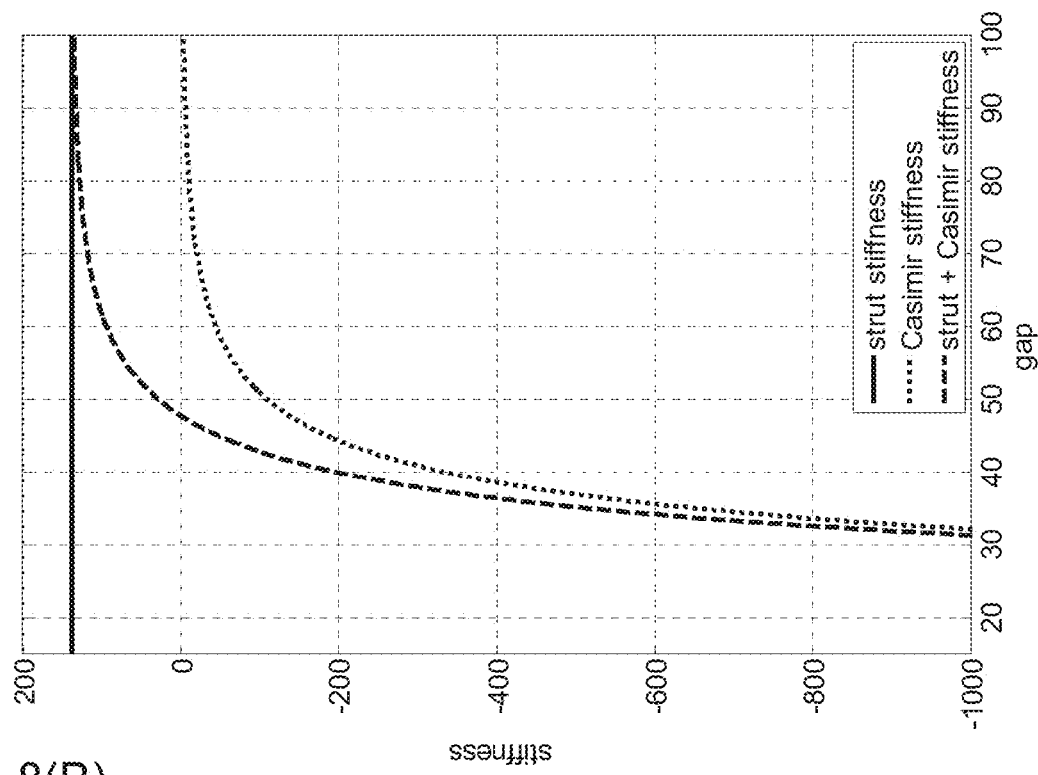
FIG. 8(B) depicts an example of estimated strut stiffness and Casimir stiffness as a function of distance between the SIL and a substrate, based on an assumption of perfectly conducting parallel plates.
Figure 8A:
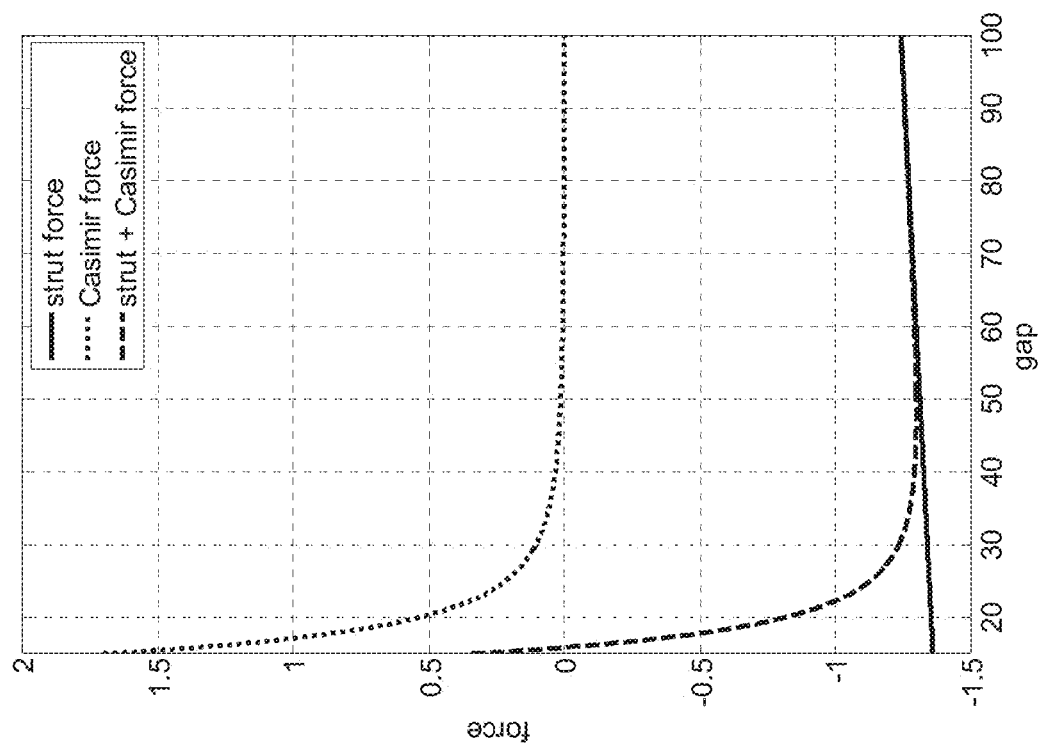
FIG. 8(A) depicts an example of estimated strut force and Casimir force as a function of distance between the SIL and a substrate, based on an assumption of perfectly conducting parallel plates.

Now referring to the graphs in FIG. 8, FIG. 8(A) shows example normalized values of strut and Casimir forces towards a target surface as a function of gap distance and FIG. 8(B) shows example normalized values of strut and Casimir stiffnesses as a function of gap distance, modeled based on the formula for parallel, perfectly conducting plates as described above. As can be seen in FIG. 8(A), the actual Casimir force may be relatively small compared to the control and strut forces. But, FIG. 8(B) shows that the Casimir stiffness rises rapidly (i.e., heads toward and/or has a negative value) as the gap between the SIL and the target surface is decreased. The gap dependent stiffness $k_{cas}(z)$ caused by the Casimir effect may negatively change closed loop behavior of the control system by counteracting the strut stiffness $k_{strut}$ as the gap between the SIL and the target surface decreases (e.g., less than 80 nm in the FIG. 8(B) example) as depicted in the graphs in FIG. 8. The disturbance in the control loop caused by Casimir stiffness, thus, adversely affects the performance of the control system by decreasing the suppression of low frequency disturbances such as target surface (e.g. substrate) vibrations within the apparatus.

As depicted in the stiffness plot in FIG. 8(B), when the gap between the SIL and the target surface is decreased further, e.g., less than 50 nm in the FIG. 8(B) example, the Casimir stiffness becomes large enough that the strut may not effectively counteract the Casimir attraction. Stability of the closed loop, therefore, should be enforced by a control system with sufficiently high bandwidth (e.g., with a bandwidth between 1 kHz and 20 kHz, for example 10 kHz). In some embodiments, for sufficiently high bandwidths, e.g., greater than about 4 kHz, a gap of about 10-30 nm or more can be maintained without stability issues. For a gap of less than about 10-30 nm, however, the Casimir stiffness may become large enough to destabilize the control loop.

Figure 9:
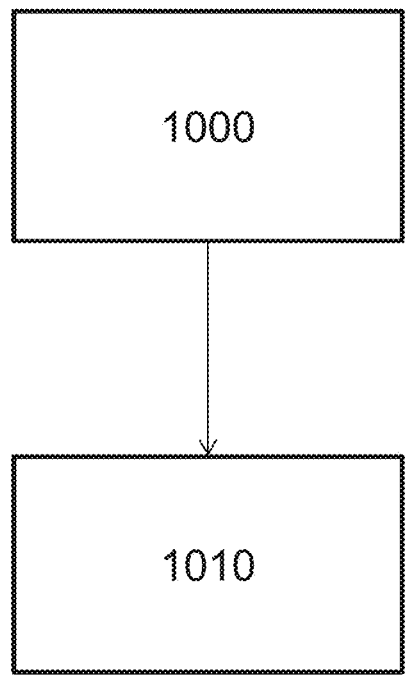
FIG. 9 depicts a flow chart of a process to position a SIL relative to a target surface.

Accordingly, in an embodiment, there is provided a method of position control of a component relative to a target surface. FIG. 9 depicts an embodiment of a method of positioning the component relative to a target surface. The method may include, at a process 1000, calculating an estimated effect of, or derived from, Casimir force acting between the component and the target surface. And, at a process 1010, the method may include compensating positioning of the component relative to the target surface using the estimated effect.

Figure 7B:
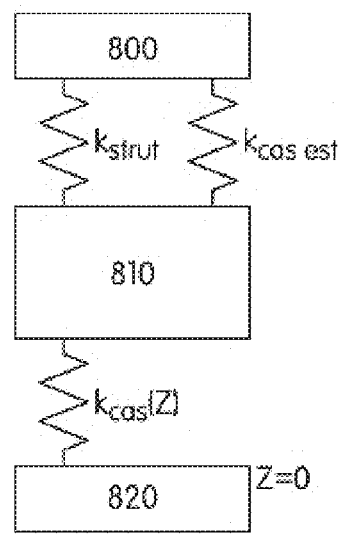
FIG. 7(B) depicts the schematic spring diagram of FIG. 7(A) modified to incorporate an estimated Casimir stiffness.
Figure 7C:
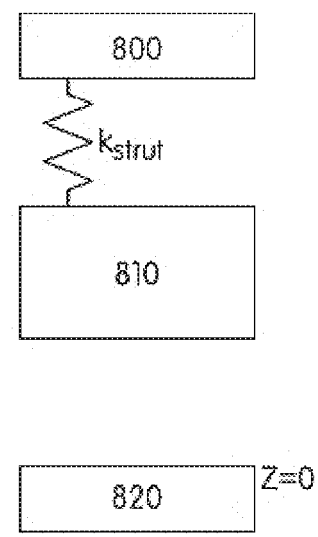
FIG. 7(C) depicts an ideal schematic spring diagram of the elements of FIGS. 7(A) and (B) after application of the estimated Casimir stiffness in FIG. 7(B)

So, referring to FIG. 7(B), FIG. 7(B) depicts the schematic spring diagram of FIG. 7(A) modified to incorporate the compensating using the estimated effect of, or derived from, Casimir force acting between the SIL 810 and the target surface 820. In this case, the estimated effect is an estimated Casimir stiffness depicted as $k_{cas\ est}(Z)$ and it is added to the strut stiffness $K_{strut}$. The compensating using the estimated Casimir stiffness depicted as $k_{cas\ est}(Z)$ should yield an ideal schematic spring diagram of the elements of FIGS. 7(A) and (B) as shown in FIG. 7(C). That is, the application of the estimated Casimir stiffness in FIG. 7(B) effectively cancels out the actual Casimir stiffness $K_{cas}(z)$ between the SIL 810 and the target surface 820 and so the SIL should have effectively only the strut stiffness $K_{strut}$ between it and the objective/frame 800.

In an embodiment, calculating an estimated effect of, or derived from, Casimir force acting between the component and the target surface may include calculating an estimated Casimir stiffness resulting from interaction between the component and the target surface. In an ideal system, the Casimir stiffness is calculated using Equation (2) above. The ideal system includes two parallel perfectly conducting surfaces separated by vacuum. In reality, for example, in case of the interaction between a SIL and a substrate, the surface of the SIL and/or the substrate surface may not be perfectly conducting, and the two surfaces may not be perfectly parallel. In some embodiments, e.g., when the substrate surface includes a periodic structure (e.g., a grating) of, e.g., a measurement target, the distance between the SIL and substrate along the SIL surface may vary. The real Casimir stiffness will, therefore, be different from the ideal Casimir stiffness.

To accommodate for differing geometry, materials or other characteristics, and/or a variation in one or more such characteristics, a constant or parameter may applied to any of the calculations described herein to approximate the effect of the differing geometry, materials, etc. and/or the variation, to the calculations using the equations described herein (or a modified version thereof). Such a constant or parameter may be determined by simulations using particular configurations of geometry, materials, etc. and/or particular variations. Thus, a particular constant or parameter may be determined for each configuration or for a plurality of configurations, or for a variation in one or more configurations. For example, a particular constant or parameter may be determined for a particular type of target surface (e.g., type of metrology/inspection target), and/or a range of variation for the particular type of target surface.

In an embodiment, the estimated Casimir stiffness may be calculated by using one or more known or measured parameters of the target surface. For example, in a use case of CD reconstruction, the geometry, and materials, of the target surface may be known or measured. Structure dependent effects of the Casimir force may, thus, be included in the calculations, including in the calculation of Casimir stiffness, to provide a more accurate estimate of Casimir force ($F_{cas\ est}(z)$) and/or stiffness ($k_{cas\ est}(z)$).

Figure 10:
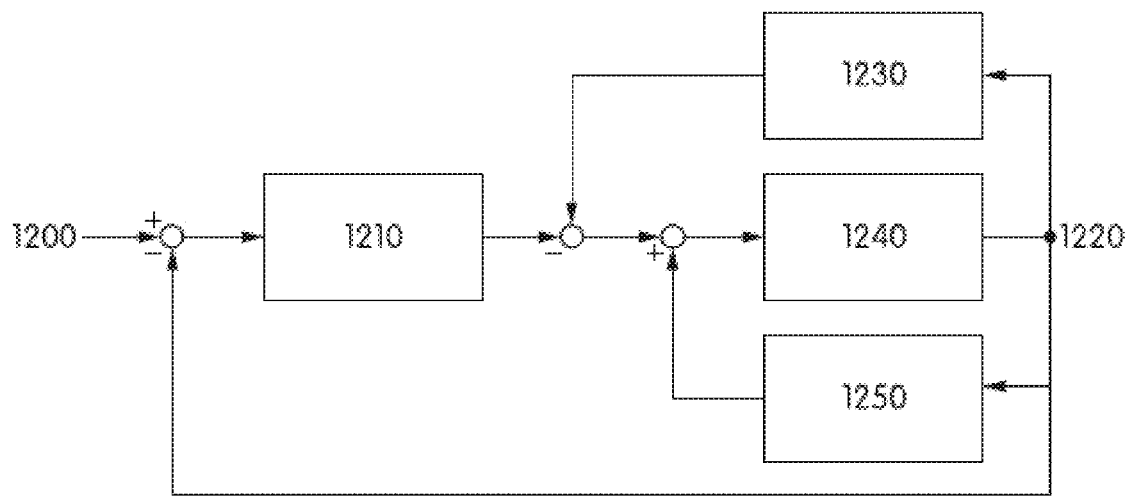
FIG. 10 depicts a schematic control loop to position a SIL relative to a target surface and a control mechanism to compensate the effect of Casimir force on a SIL.

FIG. 10 schematically depicts a schematic control loop to position a SIL relative to a target surface and a control mechanism to compensate the effect of Casimir force on the SIL. As depicted in FIG. 10, a control system 1210 actuates, for example, the SIL mass and struts 1240 according to a setpoint value 1200 to desirably achieve or maintain a particular gap Z 1220. For that gap Z, an actual/real Casimir effect 1230 is applied to the SIL. So, in an embodiment, a compensating estimated Casimir effect 1250 is applied by linearizing feedback as shown in FIG. 10. That is, the feedback effectively linearizes the control loop, where otherwise the control loop is subject to a non-linearity. In an embodiment, the estimated Casimir effect 1250 may be a calculated estimated Casimir stiffness ($k_{cas\ est}(z)$ determined using, e.g., Equation (2) or a modified version of Equation (2) that accounts for the actual materials, geometric factors, etc. The gap Z may be measured or derived from a gap error signal. In the ideal case, the Casimir stiffness calculated using Equation (2) (or the modified version of Equation (2)) is equal to the actual Casimir stiffness (i.e., the actual/real Casimir effect 1230), thereby cancelling the effect of Casimir force. So, in the ideal case, the disclosed feedback linearization, i.e., by adding estimated Casimir stiffness to the control loop, can result in obtaining the original dynamics (e.g., without the Casimir stiffness) of the control system. But, in reality, there may be an error in modelling the Casimir stiffness of the real system. Advantageously, however, linearization of the control loop reduces the sensitivity of the control loop to the deviation of the actual Casimir stiffness from its ideal value. So, in an embodiment, the techniques described herein can improve suppression of low frequency disturbances by about a factor of 10 at a gap between the SIL and the target surface selected from the range of about 10-50 nm.

For effective control of the positioning of a component relative to a surface, it is desired that the gap between the component and the surface is accurately known. In a real system, this may be difficult because the measurement signal may not be accurate, assumptions about the system (e.g., component size) may not always be valid, etc. For example, the gap between the component (e.g. SIL) and the target surface may be represented by a gap error signal (GES). If control is based on the GES, a calibration may be needed to help ensure that the gap between the component and the target surface is a certain expected gap (e.g., so as to avoid collision and to attain desired measurement conditions). For example, in the control scheme described above, an estimate of Casimir stiffness (as calculated using a formula as, e.g., described herein) may be susceptible to error when calculated using a measured gap distance (where measured gap distance means a gap distance directly measured or a gap distance derived from a measurement), without appropriate calibration.

Additionally, the measurement of the gap may be strongly dependent on the structure that is on the target surface (e.g., etched on the substrate surface). That is, the GES may be strongly dependent on the structure on the target surface. For example, if the GES is controlled at a value that corresponds to, e.g., 20 or 50 nm for a given structure, that structure might be controlled to be close to the desired 20 or 50 nm. However, another structure at that GES may already touch the SIL. So, deviation in the structure, e.g., because of a wrong user input, may cause the GES to vary significantly from an expected value. Such a deviation may result in, for example, the SIL bumping into the target surface, thus making the apparatus and the target surface susceptible to an unacceptable risk of damage.

Therefore, there is provided a method of calibrating the GES, a measured gap distance and/or a setpoint value. Additionally, there is provided a method of determining a threshold proximity between the component (e.g., SIL) and the target surface.

Figure 11:
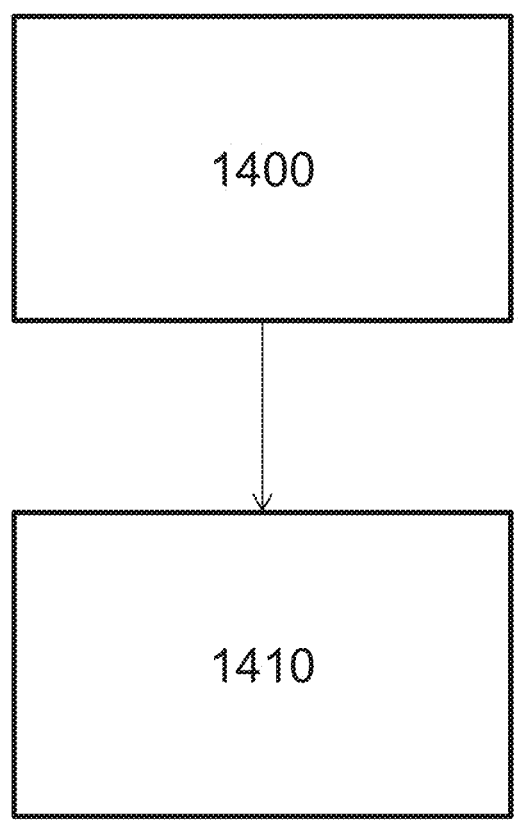
FIG. 11 depicts a flow chart of a process to determine a threshold proximity between the SIL and the target surface.

Depicted in FIG. 11 is a flowchart of a method for position control of a component relative to a surface. The method may include, at block 1400, generating a trigger signal from one or more other measurable signals in the control loop, or one or more signals derived from the one or more measurable signals (such as a control error signal, the control error signal being a measure of the difference in a measured gap distance between the component and the surface and a desired gap distance between the component and the surface), and at block 1410, evaluating whether the trigger signal passes a threshold to determine proximity of the component to the surface. In an embodiment, the control error signal is the GES or based on the GES, e.g., a difference between the setpoint value of the gap distance and the measured gap distance based on the GES.

The slope of GES at small gaps (i.e., <λ/4 nm) remains approximately constant for different structures. So, the GES is, therefore, a suitable control signal for gradually decreasing the gap between the component and the surface. Further, when gradually decreasing the gap between the SIL and target surface, the error in GES (i.e., control error) suddenly starts to increase non-linearly when it encounter instability. This instability may be attributable to Casimir stiffness or a combination of Casimir stiffness and electrostatic stiffness as discussed elsewhere herein. This instability and/or non-linearity may be used to timely determine a threshold proximity of the component to the surface. So, the control error can be used to sense the proximity of the component to the target surface, which may, for example, trigger a safety mechanism that, for example, retracts the component or discontinues its movement. In an embodiment, the retraction and/or discontinuance of movement can be distributed over the objective and SIL stage in a dual stage arrangement depending on, e.g., the reaction time and/or retraction range. Alternatively or additionally to the control error, one or more other measurable signals in the control loop, or one or more signals derived from the one or more measurable signals, can be used as a trigger signal.

In an embodiment, the GES signal can be a normalized signal with respect to its far field intensity. As a result, the normalized GES signal value for control may be between 0 and 1, substantially independent of the properties of the illumination.

In an embodiment, the trigger signal relatively suddenly increases or decreases as the instability approaches. The sudden change is caused by the relatively very non-linear characteristics of the Casimir stiffness and/or electrostatic stiffness given by Equations (2) and (4), respectively. An appropriate threshold may be applied to the signal to determine the point where the instability occurs or a point just in advance of the instability.

In an embodiment, the trigger signal may be, for a certain moving time window (e.g., like a moving average), a maximum absolute value of the signal (e.g., control error). In an embodiment, the trigger signal may be a norm-based quantification of the size of the signal, such as the maximum absolute value of the signal (e.g., control error) for a moving time window of that signal. Other examples of trigger signal include a root-mean-square (RMS) value of the signal (e.g., control error) for a moving window of that signal, and/or energy content (e.g., RMS) of the signal (e.g., control error) for one or more specific frequencies indicative of control loop instability for a moving window of that signal. In an embodiment, the moving window is in the range of 0-100 ms, for example, 0-20 ms, for example 1 ms, 2 ms or 10 ms. The applied window size can depend on the approach speed of the SIL with respect to the surface and the frequency content of the relative vibrations between the SIL and the surface. The trigger signal may be normalized in some embodiments. By generating the trigger signal based on relative change in the control error, the influence of vibrations (e.g., of the substrate or the inspection apparatus) on the control error may be cancelled out.

Figure 12:
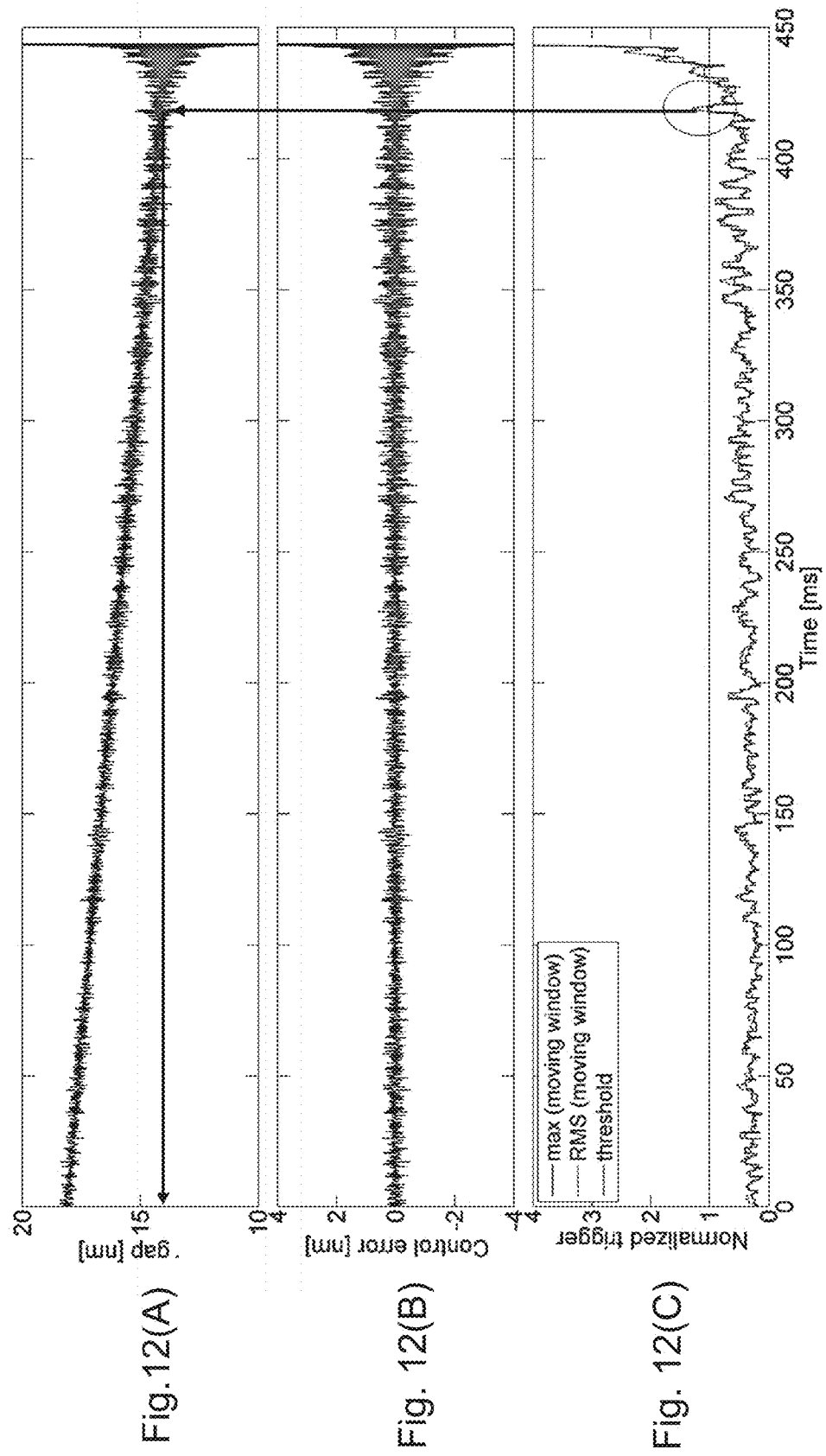
FIGS. 12(A), 12(B) and 12(C) depict simulation results showing gap distance, control error and various normalized trigger signals that can be used to detecting control instability.

FIG. 12 depicts graphed simulation results showing gap distance (FIG. 12(A)), control error (FIG. 12(B)), and two normalized trigger signals (FIG. 12(C)). In this example, as seen in FIG. 12(A), the gap is slowly reduced from about 18 nm to about 14 nm. In FIG. 12(C), it can be seen that the trigger signals are able to detect the control instability around 440 ms in the control error signal when the trigger signal passes the threshold of 1 already at around 420 ms. In this embodiment, the corresponding gap distance is about 14 nm. As discussed elsewhere herein, the control instability is encountered due to Casimir forces, electrostatic forces, or a combination thereof. In many instances, the electrostatic force is unknown because the voltage difference between the SIL and the substrate is unknown. But, electrostatic forces, where present, are an additional component to the Casimir forces. So, a threshold based on Casimir forces alone is effective as, for example, a safety trigger, even if electrostatic forces are present.

The encountering of instability is an indicator of the component (e.g., SIL) being too close to the target surface and so the component is at risk of crashing into the target surface. Therefore, in an optical system using a SIL, increasing the gap between the SIL and the target surface may be an action taken when an instability of the control loop is encountered. However, in some embodiments, other actions such as stopping the motion of the SIL and/or analyzing the structure on the target surface interacting with the SIL may be performed.

Ideally, the measured gap distance and the actual gap distance are the same. In reality, however, the measured gap distance may be different from the actual gap distance because of various reasons. The measured gap distance, a gap error signal and/or a setpoint value, in such cases, may need to be corrected using a calibration or correction factor. As such, a method for calibrating a measured gap distance, a gap error signal and/or a setpoint value is disclosed herein.

As noted above, recognizing that an instability in the control loop (which is manifested in the GES) occurs when a component closely approaches a surface and that such instability arises from the microscopic forces at play at such small distances, the instability can be used as a means to calibrate the gap error signal, a measured gap distance and/or a setpoint value.

Indeed, ideally, if the structure is known, the GES is known. So, there may not be any need for calibration based on Casimir force. But, if the structure is not fully known, the GES may have a (significant) error. But, Casimir stiffness is expected to have a small error due to its strong dependency on the gap and relatively weak dependency on the structure. Hence, the Casimir stiffness can be a way to calibrate, for example, the GES where, for example, the structure is not fully known.

So, in an embodiment, for a component of known surface area, the Casimir stiffness and/or electrostatic stiffness, given by Equations (2) and (4) respectively, is dependent only on the gap between the component and the surface. So, an estimated value of the absolute gap between the component and the surface (i.e., an estimated gap distance) can be calculated using Equation (2) and/or Equation (4) from a value of stiffness that destabilizes the control loop for positioning the component. As discussed above, the calculated values may be altered by a constant or parameter to account for one or more characteristics of the component and/or surface, and/or variation in the one or more characteristics. The constant or parameter may be derived by simulation and/or calibration.

Further, a gap signal indicative of the gap distance between the component and the surface may be evaluated to identify an instability in the control loop, which instability is manifested in the gap signal. That instability occurs due to the microscopic forces. The gap distance at the instability in the gap signal can be termed as a reference gap distance, e.g., the about 14 nm gap distance identified in FIG. 12. In an embodiment, the gap signal may be, for example, the GES, or a control error signal from the control loop used for positioning the component relative to the surface, or other measured or derived signal from the control loop as discussed above. In some embodiments, the gap signal may be further derived from the control error signal (e.g., the trigger signal discussed above). For example, the gap signal may be a norm-based quantification of the size of the measured or derived signal for a moving window of that signal, such as a maximum absolute value of the measured or derived signal (e.g., control error) for a moving window of that signal, a root-mean-square value of the measured or derived signal (e.g., control error) for a moving window of that signal, and/or energy content of the measured or derived signal for a specific frequency indicative of control loop instability for a moving window of that signal.

The reference gap distance and the estimated gap distance are then evaluated against each other. In an ideal system, the reference gap distance is equal to the estimated gap distance that is calculated based on the Casimir and/or electrostatic stiffness formulas. So, if they are equal, the system is already calibrated. However, since a system may deviate from ideal behavior, the reference gap distance may be different from the estimated gap distance. Accordingly, a correction or calibration factor may, thus, be determined where the reference gap distance and the estimated gap distance are different. For example, a correction or calibration factor may be determined from the difference between the reference gap distance and the estimated gap distance and may be applied to the GES signal, to a measured gap distance, and/or to a setpoint value of the control loop. As another example, the corresponding GES values can be set as a lower set point (i.e., threshold) for the given structure on the substrate, and so be used to, for example, trigger a safety mechanism for avoiding the crashing of the component with the surface.

The correction or calibration factor may be determined once per metrology/inspection target, per substrate, or per batch of substrates, dependent on the expected structure variations between targets/substrates/batches.

In an embodiment, it may be desirable to isolate the Casimir force as being the only significant force causing the instability in the GES of the component and so only the reference distance calculated for the Casimir effect may be needed. To do so, in an embodiment, a voltage difference between the component and the surface may be eliminated, thereby eliminating the electrostatic stiffness attributable to the voltage difference between the component and the surface. The voltage difference may be eliminated by any known method such as providing a conductive coating on the surface of component and/or the target surface and grounding both the surfaces.

In an embodiment, instead of eliminating the voltage difference between the component and the surface, a known voltage difference may be provided or the voltage difference may be determined. In such an embodiment, if the area of the surface of the component interacting with the target surface is known, the total stiffness (i.e., combination of electrostatic stiffness and Casimir stiffness) is still dependent on the gap between the component and the surface. Thus, for a known or measured voltage difference, the reference distance can still be calculated based on a value of stiffness that destabilizes the gap signal. Because the non-linearity for the electrostatic stiffness is lower than the non-linearity of the Casimir stiffness (power of −3 as against power of −5), the calculation of gap distance using the combination of electrostatic stiffness and Casimir stiffness may not be as robust as using the Casimir stiffness alone. The known voltage difference should be sufficiently low to avoid voltage breakdown between the component and the surface.

Figure 13:
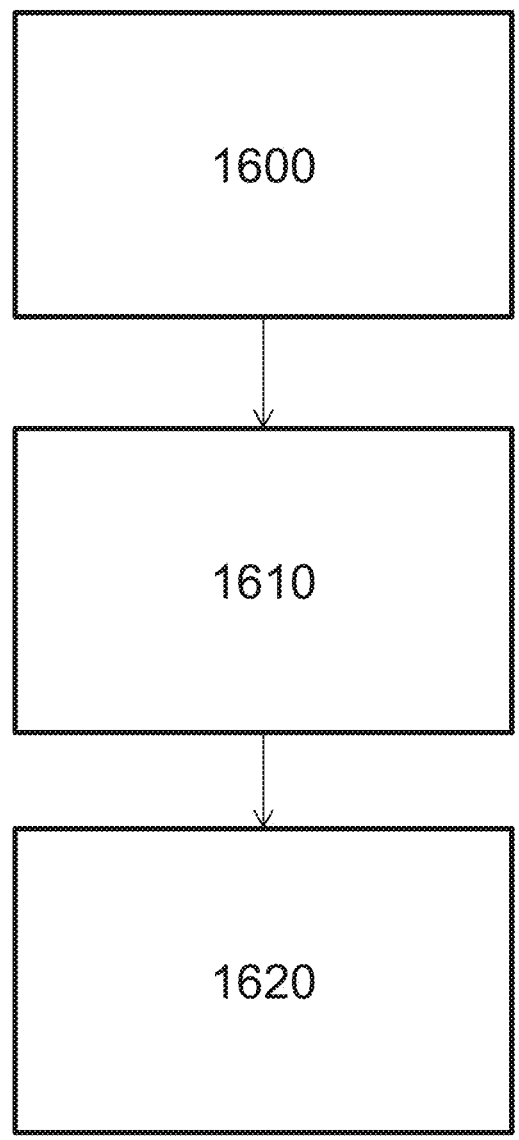
FIG. 13 depicts a flow chart of a process to calibrate a gap error signal, a measured gap distance and/or a setpoint value.

FIG. 13 depicts an example flow chart of a process to calibrate a measured gap distance, a gap error signal and/or a setpoint value. The method includes, at block 1600, for a value of a stiffness that destabilizes a control signal for positioning a component relative to a surface, calculating an estimated gap distance between a component and a surface based on Casimir and/or electrostatic stiffness between the component and the surface. At block 1610, a gap signal related to a gap distance between the component and the surface is evaluated to identify an instability in the gap signal, the gap distance at the instability being a reference gap distance. At block 1620, the reference gap distance is evaluated against the estimated gap distance to arrive at a correction factor for positioning of the component relative to the surface.

While the various embodiments herein primarily describe position control of a SIL relative to a substrate/target surface, the disclosed methods and apparatus may be used to control the position of any component, such as a microcantilever, relative to any surface.

As described above, in an embodiment, there are provided various techniques to control the gap by a technique based on one or more specific measurement signals. The techniques have particular applicability in an optical metrology or inspection apparatus such as a scatterometer, an alignment sensor (which determine alignment between alignment mark), an encoder or interferometer (which enable position measurement), and/or a height or level sensor (which enables measuring of the position of a surface), but can be applied in other applications of SILs or in other applications where an object is positioned and/or maintained very close to another object (e.g., in the below 400 nm range). The technique need not be applied exclusively, and could be applied in combination with one or more other techniques, including one or more techniques discussed in the cited documents.

Any controllers or control systems described herein may each or in combination be operable when the one or more computer programs are read by one or more computer processors located within at least one component of the lithographic apparatus. The controllers or control systems may each or in combination have any suitable configuration for receiving, processing, and sending signals. One or more processors are configured to communicate with the at least one of the controllers or control systems. For example, each controller or control system may include one or more processors for executing the computer programs that include machine-readable instructions for the methods described above. The controllers or control systems may include a data storage medium for storing such computer programs, and/or hardware to receive such medium. So the controller(s) or control system(s) may operate according the machine readable instructions of one or more computer programs.

Although specific reference may have been made in this text to the use of embodiments of the invention in the context of metrology or inspection apparatus used to inspect or measure items in association with, e.g., optical lithography, it will be appreciated that the methods and apparatus described herein may be used in other applications, for example imprint lithography, the use or manufacture of integrated optical systems, the use or manufacture of guidance and detection patterns for magnetic domain memories, the use or manufacture of flat-panel displays, the use or manufacture of liquid-crystal displays (LCDs), the use or manufacture of thin film magnetic heads, etc. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Further embodiments are described in below numbered clauses:

1. A method of position control of a component relative to a surface, the method comprising:
    calculating an estimated effect of, or derived from, proximity forces acting between the component and the surface; and
    compensating positioning of the component relative to the surface using the estimated effect.
2. The method of clause 1, wherein calculating the estimated effect comprises calculating an estimated effect derived from Casimir force and/or electro-magnetic forces between the component and the surface.
3. The method of clause 2, wherein calculating the estimated effect derived from Casimir force and/or electro-magnetic forces between the component and the surface comprises calculating a proximity stiffness between the component and the surface.
4. The method of any of clauses 1-3, wherein the compensating comprises a feedback based on a measurement of the gap to linearize a control loop for relative movement between the component and the surface.
5. The method of any of clauses 1-4, wherein calculating the estimated effect comprises calculating the estimated effect using a formula wherein the estimated effect is proportional to $1/z^3$, $1/z^4$, or $1/z^5$.
6. The method of any of clauses 1-5, wherein calculating the estimated effect comprises calculating the estimated effect based on a measured gap distance between the component and the surface.
7. The method of clause 6, wherein the measured gap distance is a gap distance derived from a measured gap error signal.
8. A method, comprising:
    for a value of a proximity force or stiffness that destabilizes a control signal for positioning a component relative to a surface, calculating an estimated gap distance between the component and the surface based on proximity force or stiffness between the component and the surface;

evaluating a gap signal related to a gap distance between the component and the surface to identify an instability in the gap signal, the gap distance at the instability being a reference gap distance; and evaluating the reference gap distance against the estimated gap distance to arrive at a correction factor for positioning of the component relative to the surface.

9. The method of clause 8, wherein the gap signal comprises a trigger signal generated from a measured signal in a control loop of the component, or from a signal derived from the measured signal in the control loop.

10. The method of clause 9, wherein the trigger signal is generated from a control error signal, the control error signal being a measure of the difference in a measured gap between the component and the surface and a desired gap between the component and the surface.

11. The method of clause 9 or clause 10, wherein the trigger signal comprises a value for a moving window of the measured or derived signal.

12. The method of clause 11, wherein the value for the moving window comprises a maximum absolute value of the measured or derived signal, a root-mean-square value of the measured or derived signal, energy content of the measured or derived signal for a specific frequency indicative of control loop instability and/or other norm-based quantification of the size of the measured or derived signal.

13. The method of any of clauses 8-12, wherein the correction factor comprises a correction to the gap signal, to a measured distance of the gap, and/or to a setpoint value of a control loop for relative movement between the component and the surface.

14. A method of position control of a component relative to a surface, the method comprising:

calculating an estimated effect of, or derived from, Casimir force acting between the component and the surface; and compensating positioning of the component relative to the surface using the estimated effect.

15. The method of clause 14, wherein calculating the estimated effect comprises calculating an estimated effect derived from Casimir force between the component and the surface.

16. The method of clause 15, wherein calculating the estimated effect derived from Casimir force between the component and the surface comprises calculating a Casimir stiffness between the component and the surface.

17. The method of clause 14, wherein the compensating comprises a feedback based on a measurement of the gap to linearize a control loop for relative movement between the component and the surface.

18. The method of clause 14, wherein calculating the estimated effect comprises calculating the estimated effect using a formula wherein the estimated effect is proportional to $1/z^3$, $1/z^4$, or $1/z^5$.

19. The method of clause 14, wherein calculating the estimated effect comprises calculating the estimated effect based on a measured gap distance between the component and the surface.

20. The method of clause 19, wherein the measured gap distance is a gap distance derived from a measured gap error signal.

21. A method of position control of a component relative to a surface, the method comprising:

generating a trigger signal from a measured signal in a control loop of the component, or from a signal derived from the measured signal in the control loop; and evaluating whether the trigger signal passes a threshold to determine proximity of the component to the surface.

22. The method of clause 21, wherein generating the trigger signal comprises derivation of the trigger signal from a control error signal, the control error signal being a measure of the difference in a measured gap between the component and the surface and a desired gap between the component and the surface.

23. The method of clause 21 or clause 22, wherein the trigger signal comprises a value for a moving window of the measured or derived signal.

24. The method of clause 23, wherein the value for the moving window comprises a maximum absolute value of the measured or derived signal, a root-mean-square value of the measured or derived signal, energy content of the measured or derived signal for a specific frequency indicative of control loop instability and/or other norm-based quantification of the size of the measured or derived signal.

25. The method of any of clauses 21-14, further comprising activating a mechanism to increase the gap between the component and the surface when the trigger signal passes the threshold.

26. The method of any of clauses 21-25, wherein the threshold corresponds to the occurrence, or advent, of instability in the measured or derived signal.

27. A method, comprising:

for a value of a Casimir and/or electrostatic force or stiffness that destabilizes a control signal for positioning a component relative to a surface, calculating an estimated gap distance between the component and the surface based on Casimir and/or electrostatic force or stiffness between the component and the surface;

evaluating a gap signal related to a gap distance between the component and the surface to identify an instability in the gap signal, the gap distance at the instability being a reference gap distance; and evaluating the reference gap distance against the estimated gap distance to arrive at a correction factor for positioning of the component relative to the surface.

28. The method of clause 27, wherein the gap signal comprises a trigger signal generated from a measured signal in a control loop of the component, or from a signal derived from the measured signal in the control loop.

29. The method of clause 28, wherein the trigger signal is generated from a control error signal, the control error signal being a measure of the difference in a measured gap between the component and the surface and a desired gap between the component and the surface.

30. The method of clause 28 or clause 29, wherein the trigger signal comprises a value for a moving window of the measured or derived signal.

31. The method of clause 30, wherein the value for the moving window comprises a maximum absolute value of the measured or derived signal, a root-mean-square value of the measured or derived signal, energy content of the measured or derived signal for a specific frequency indicative of control loop instability and/or other norm-based quantification of the size of the measured or derived signal.

32. The method of any of clauses 27-31, comprising calculating the estimated gap distance between the component and the surface based on Casimir force or stiffness between the component and the surface.

33. The method of any of clauses 27-32, wherein the correction factor comprises a correction to the gap signal, to a measured distance of the gap, and/or to a setpoint value of a control loop for relative movement between the component and the surface.

34. A method of position control of a component relative to a surface, the method comprising:
    calculating an estimated effect of Casimir stiffness acting between the component and the surface based on a measured gap distance between the component and the surface; and
    using the estimated effect of Casimir stiffness to compensate actual Casimir stiffness of the positioning of the component relative to the surface.

35. The method of any of the preceding clauses, wherein the component comprises a solid immersion lens and the surface comprises a measurement target surface.

36. The method of any of the preceding clauses, further comprising positioning the component within 1 nm to 50 nm of the surface.

37. A method of manufacturing devices wherein a device pattern is applied to a series of substrates using a lithographic process, the method including inspecting at least a target formed as part of or beside the device pattern on at least one of the substrates using the method of any of clauses 14-36, and controlling the lithographic process for later substrates in accordance with the result of the method.

38. A non-transitory computer program product comprising machine-readable instructions for causing a processor to cause performance of the method of any of clauses 14-37.

39. A system comprising:
    an inspection apparatus configured to provide a beam on a measurement target on a substrate and to detect radiation redirected by the target to determine a parameter of a lithographic process; and
    the non-transitory computer program product of clause 38.

40. The system of clause 39, further comprising a lithographic apparatus comprising a support structure configured to hold a patterning device to modulate a radiation beam and a projection optical system arranged to project the modulated onto a radiation-sensitive substrate.

The terms "radiation" and "beam" used herein encompass all types of electromagnetic radiation, including ultraviolet (UV) radiation (e.g. having a wavelength of less than about 400 nm and greater than about 20 nm, or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic; electromagnetic and electrostatic optical components.

While specific embodiments of the invention have been described above, it will be appreciated that the invention may be practiced otherwise than as described. For example, an embodiment of the invention may take the form of a computer program containing one or more sequences of machine-readable instructions describing a method as disclosed herein, or a non-transitory data storage medium (e.g. semiconductor memory, magnetic or optical disk, etc.) or a transitory medium having such a computer program therein. Further, the machine readable instruction may be embodied in two or more computer programs. The two or more computer programs may be stored on one or more different memories and/or data storage media.

The descriptions above are intended to be illustrative, not limiting. Thus, it will be apparent to one skilled in the art that modifications may be made to the invention as described without departing from the scope of the claims set out below.

What is claimed is:

1. A method of position control, the method comprising:
    calculating an estimated effect of, or derived from, Casimir force acting between a component and a surface and a value of a compensation, based on the estimated effect, to modify the positioning of the component relative to the surface to correct for the estimated effect; and
    compensating, based on the compensation value, positioning of the component relative to the surface.

2. The method of claim 1, wherein calculating the estimated effect comprises calculating an estimated effect derived from Casimir force between the component and the surface.

3. The method of claim 2, wherein calculating the estimated effect derived from Casimir force between the component and the surface comprises calculating a Casimir stiffness between the component and the surface.

4. The method of claim 1, wherein the compensating comprises a feedback based on a measurement of the gap to linearize a control loop for relative movement between the component and the surface.

5. The method of claim 1, wherein calculating the estimated effect comprises calculating the estimated effect using a formula wherein the estimated effect is proportional to $1/z^3$, $1/z^4$, or $1/z^5$, wherein z corresponds to a distance between the component and the surface.

6. The method of claim 1, wherein calculating the estimated effect comprises calculating the estimated effect based on a measured gap distance between the component and the surface.

7. The method of claim 6, wherein the measured gap distance is a gap distance derived from a measured gap error signal.

8. The method of claim 1, wherein the component comprises a solid immersion lens and the surface comprises a measurement target surface.

9. The method of claim 1, further comprising positioning the component within 1 nm to 50 nm of the surface.

10. A method of manufacturing devices wherein a device pattern is applied to a series of substrates using a lithographic process, the method including inspecting at least a target formed as part of or beside the device pattern on at least one of the substrates using the method of claim 1, and controlling the lithographic process for later substrates in accordance with the result of the method.

11. A non-transitory computer program product comprising machine-readable instructions for causing a processor to cause performance of at least:

calculation of an estimated effect of, or derived from, Casimir force acting between a component and a surface and a value of a compensation, based on the estimated effect, to modify the positioning of the component relative to the surface to correct for the estimated effect; and compensation, based on the compensation value, of positioning of the component relative to the surface.

12. A system comprising:

an inspection apparatus configured to provide a beam on a measurement target on a substrate and to detect radiation redirected by the target to determine a parameter of a lithographic process; and the non-transitory computer program product of claim 11.

13. The computer program product of claim 11, wherein the instructions configured to cause performance of the calculation of the estimated effect are configured to cause performance of calculation of an estimated effect derived from Casimir force between the component and the surface.

14. The computer program product of claim 13, wherein the instructions configured to cause performance of the calculation of the estimated effect derived from Casimir force between the component and the surface are configured to cause performance of calculation of a Casimir stiffness between the component and the surface.

15. The computer program product of claim 11, wherein the instructions configured to cause performance of the compensation are further configured to cause a feedback based on a measurement of the gap to linearize a control loop for relative movement between the component and the surface.

16. The computer program product of claim 11, wherein the instructions configured to cause performance of the calculation of the estimated effect are further configured to cause performance of calculation of the estimated effect using a formula wherein the estimated effect is proportional to $1/z^3$, $1/z^4$, or $1/z^5$, wherein z corresponds to a distance between the component and the surface.

17. The computer program product of claim 11, wherein the instructions configured to cause performance of the calculation of the estimated effect are further configured to cause performance of calculation of the estimated effect based on a measured gap distance between the component and the surface.

18. The computer program product of claim 17, wherein the measured gap distance is a gap distance derived from a measured gap error signal.

19. The computer program product of claim 11, wherein the component comprises a solid immersion lens and the surface comprises a measurement target surface.

20. The computer program product of claim 11, wherein the instructions are further configured to cause positioning of the component within 1 nm to 50 nm of the surface.

21. A method of position control, the method comprising:

calculating an estimated Casimir stiffness acting between a component and a surface based on a measured gap distance between the component and the surface and a value of a compensation to modify the positioning of the component relative to the surface to correct for the estimated effect; and compensating, based on the compensation value, positioning of the component relative to the surface.

22. The method of claim 21, wherein the component comprises a solid immersion lens and the surface comprises a measurement target surface.

23. The method of claim 21, comprising positioning of the component within 1 nm to 50 nm of the surface.

24. A non-transitory computer program product comprising machine-readable instructions for causing a processor to cause performance of at least:

calculation of an estimated Casimir stiffness acting between a component and a surface based on a measured gap distance between the component and the surface and a value of a compensation to modify the positioning of the component relative to the surface to correct for the estimated effect; and compensation, based on the compensation value, of positioning of the component relative to the surface.

25. The computer program product of claim 24, wherein the component comprises a solid immersion lens and the surface comprises a measurement target surface.

26. The computer program product of claim 24, wherein the instructions are further configured to cause positioning of the component within 1 nm to 50 nm of the surface.

* * * * *